(12) United States Patent
Vaddiraju et al.

(10) Patent No.: US 11,512,384 B2
(45) Date of Patent: Nov. 29, 2022

(54) ANALYTE SENSORS AND METHODS FOR FABRICATING ANALYTE SENSORS

(71) Applicant: MEDTRONIC MINIMED, INC., Northridge, CA (US)

(72) Inventors: Santhisagar Vaddiraju, Plymouth, MN (US); Dennis Slomski, Porter Ranch, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 730 days.

(21) Appl. No.: 15/900,630

(22) Filed: Feb. 20, 2018

(65) Prior Publication Data

US 2018/0325430 A1    Nov. 15, 2018

Related U.S. Application Data

(60) Provisional application No. 62/504,670, filed on May 11, 2017.

(51) Int. Cl.
*C23C 14/20* (2006.01)
*C23C 14/58* (2006.01)
(Continued)

(52) U.S. Cl.
CPC ........ *C23C 14/205* (2013.01); *A61B 5/14532* (2013.01); *A61B 5/14865* (2013.01); *B23K 26/36* (2013.01); *B41M 1/06* (2013.01); *B41M 1/10* (2013.01); *B41M 1/12* (2013.01); *B41M 5/0047* (2013.01); *C23C 14/34* (2013.01); (Continued)

(58) Field of Classification Search
CPC ..... C23C 14/14; C23C 14/34; C23C 14/5873; C23C 14/205; C23C 14/5813; A61B 5/1486; A61B 5/14532; A61B 5/1473; A61B 5/14865; B23K 26/36; B41M 5/0047; B41M 1/10; B41M 1/12; B41M 1/06; G01N 27/327; G01N 27/3271; G01N 27/3272; G01N 27/3273; G01N 27/3277; G01N 27/4115
See application file for complete search history.

(56) References Cited

U.S. PATENT DOCUMENTS

4,755,173 A    7/1988 Konopka et al.
5,391,250 A    2/1995 Cheney, II et al.
(Continued)

*Primary Examiner* — Michael A Band
(74) *Attorney, Agent, or Firm* — Lorenz & Kopf, LLP (57) ABSTRACT

Analyte sensors and methods for fabricating analyte sensors are provided. In an exemplary embodiment, a method for fabricating a planar flexible analyte sensor includes sputtering platinum onto a polyester base layer to form a layer of platinum. The method includes patterning the layer of platinum to form working electrodes and additional electrodes. Further, the method includes forming an insulating dielectric layer over the base layer, wherein the insulating dielectric layer is formed with openings exposing portions of the working electrodes and portions of the additional electrodes. Also, the method includes partially singulating individual sensors from the base layer, wherein each individual sensor is connected to the base layer by a tab. The method further includes depositing an enzyme layer over the exposed portions of the working electrodes and coating the working electrodes with a glucose limiting membrane.

10 Claims, 3 Drawing Sheets

(51) Int. Cl.
*C23C 14/34* (2006.01)
*A61B 5/145* (2006.01)
*A61B 5/1486* (2006.01)
*B23K 26/36* (2014.01)
*B41M 1/06* (2006.01)
*B41M 1/10* (2006.01)
*B41M 1/12* (2006.01)
*B41M 5/00* (2006.01)
*G01N 27/327* (2006.01)
*G01N 27/411* (2006.01)
*C12Q 1/00* (2006.01)
*G01N 27/40* (2006.01)

(52) U.S. Cl.
CPC ...... *C23C 14/5813* (2013.01); *C23C 14/5873* (2013.01); *G01N 27/327* (2013.01); *G01N 27/3271* (2013.01); *G01N 27/3273* (2013.01); *G01N 27/3277* (2013.01); *G01N 27/4115* (2013.01); *A61B 5/1486* (2013.01); *A61B 2562/0209* (2013.01); *A61B 2562/125* (2013.01); *C12Q 1/006* (2013.01); *G01N 27/40* (2013.01)

(56) References Cited

U.S. PATENT DOCUMENTS

| | | |
|---|---|---|
| 5,485,408 A | 1/1996 | Blomquist |
| 5,522,803 A | 6/1996 | Teissen-Simony |
| 5,651,869 A | 7/1997 | Yoshioka et al. |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2004/0074785 A1* | 4/2004 | Holker ................ A61B 5/1486 205/777.5 |
| 2007/0123819 A1 | 5/2007 | Mernoe et al. |
| 2007/0278097 A1 | 12/2007 | Bhullar et al. |
| 2010/0160861 A1 | 6/2010 | Causey, III et al. |
| 2010/0252452 A1 | 10/2010 | Newman et al. |
| 2012/0186997 A1 | 7/2012 | Li et al. |
| 2014/0243634 A1 | 8/2014 | Huang et al. |
| 2014/0296823 A1* | 10/2014 | Ward ................ A61B 5/1473 604/504 |

* cited by examiner

ANALYTE SENSORS AND METHODS FOR FABRICATING ANALYTE SENSORS

CROSS-REFERENCE TO RELATED APPLICATION(S)

This application claims the benefit of U.S. Provisional Patent Application Ser. No. 62/504,670 filed May 11, 2017, the entire content of which is incorporated by reference herein.

TECHNICAL FIELD

Embodiments of the subject matter described herein relate generally to sensors for monitoring analyte levels in patients and to methods for fabricated such sensors. More particularly, embodiments of the subject matter relate to glucose sensors, such as for monitoring blood glucose level continuously, or substantially continuously.

BACKGROUND

The pancreas of a normal healthy person produces and releases insulin into the blood stream in response to elevated blood plasma glucose levels. Beta cells (β-cells), which reside in the pancreas, produce and secrete insulin into the blood stream as it is needed. If β-cells become incapacitated or die, a condition known as Type 1 diabetes mellitus (or in some cases, if β-cells produce insufficient quantities of insulin, a condition known as Type 2 diabetes), then insulin may be provided to a body from another source to maintain life or health.

Traditionally, because insulin cannot be taken orally, insulin has been injected with a syringe. More recently, the use of infusion pump therapy has been increasing in a number of medical situations, including for delivering insulin to diabetic individuals. For example, external infusion pumps may be worn on a belt, in a pocket, or the like, and they can deliver insulin into a body via an infusion tube with a percutaneous needle or a cannula placed in subcutaneous tissue.

As of 1995, less than 5% of Type 1 diabetic individuals in the United States were using infusion pump therapy. Currently, over 7% of the more than 900,000 Type 1 diabetic individuals in the U.S. are using infusion pump therapy. The percentage of Type 1 diabetic individuals that use an infusion pump is growing at a rate of over 2% each year. Moreover, the number of Type 2 diabetic individuals is growing at 3% or more per year, and growing numbers of insulin-using Type 2 diabetic individuals are also adopting infusion pumps. Additionally, physicians have recognized that continuous infusion can provide greater control of a diabetic individual's condition, so they too are increasingly prescribing it for patients.

An infusion pump system may include an infusion pump that is automatically and/or semi-automatically controlled to infuse insulin into a patient. The infusion of insulin may be controlled to occur at times and in amounts that are based, for example, on blood glucose measurements obtained from an embedded analyte sensor, such as a glucose sensor, in real-time.

There are two main types of blood glucose monitoring systems used by patients: single point or non-continuous and continuous. Non-continuous systems consist of meters and tests strips and require blood samples to be drawn from fingertips or alternate sites, such as forearms and legs. These systems rely on lancing and manipulation of the fingers or alternate blood draw sites, which can be extremely painful and inconvenient, particularly for children.

Continuous monitoring sensors are generally implanted subcutaneously and measure glucose levels in the interstitial fluid at various periods throughout the day, providing data that shows trends in glucose measurements over a short period of time. These sensors are painful during insertion and usually require the assistance of a health care professional. Further, these sensors are intended for use during only a short duration (e.g., monitoring for a matter of days to determine a blood sugar pattern). Subcutaneously implanted sensors may lead to infection and immune response complications. Another major drawback of currently available continuous monitoring devices is that they require frequent, often daily, calibration using blood glucose results that must be obtained from painful finger-sticks using traditional meters and test strips. This calibration, and recalibration, is required to maintain sensor accuracy and sensitivity, but it can be cumbersome as well as painful.

A typical glucose sensor works according to the following chemical reactions:

Equation 1

Equation 2

In equation 1, the glucose oxidase is used to catalyze the reaction between glucose and oxygen to yield gluconic acid and hydrogen peroxide ($H_2O_2$). The hydrogen peroxide reacts electrochemically as shown in Equation 2 and the resulting current can be measured by a potentiostat. These reactions, which occur in a variety of oxidoreductases known in the art, are used in a number of sensor designs.

In the case of three electrode design (working, counter and reference electrode), the reference electrode is not consumed and the as produced 02 (Equation 2) is reduced at the counter electrode as per reaction (3)

$$O_2 + 2H_2O + 4e^- \rightarrow 4OH^+ \qquad (3)$$

In the case of two electrode design (working and reference electrode only), the following reaction occurs at the reference electrode $$AgCl + e^- \rightarrow Ag + Cl^- \qquad (4)$$

Here it is worth discussing the relative merits of the 2-electrode and 3-electrode designs. In the case of 3-electrode design, oxygen is consumed at the counter electrode which is also needed for the glucose oxidase (Equation 1). However, the Ag/AgCl reference remains stable; albeit sensor dependence on oxygen increases. In the case of 2-electrode design, sensor dependence of oxygen is lowered; albeit the AgCl is consumed over time (as per Equation 4) and thus one must provide enough amount of AgCl adequate for lifetime of the sensor.

As analyte sensor technology matures and new applications for sensor technology are developed, there is a need for improved analyte sensors, such as for continuous monitoring sensors for use over longer durations. Also, there is a need to develop advanced processes for sensor fabrication that will yield a factory calibrated analyte sensor without need for further external calibrations.

Further, there is a need for low cost, large scale production of analyte sensors, such as glucose sensors. Conventional batch processing is not amenable to high volume production or to significant cost reductions.

Accordingly, it is desirable to have an improved analyte sensor and related fabrication method that address the shortcomings of traditional sensor systems. Furthermore, other desirable features and characteristics will become apparent from the subsequent detailed description and the appended claims, taken in conjunction with the accompanying drawings and the foregoing technical field and background.

BRIEF SUMMARY

Analyte sensors and methods for fabricating analyte sensors are provided. In an exemplary embodiment, a planar flexible analyte sensor includes a flexible base layer and a first electrode formed from a layer of sputtered platinum on the base layer. Also, the analyte sensor includes an insulating dielectric layer over the base layer, wherein the insulating dielectric layer leaves a portion of the first electrode exposed. Further, the analyte sensor includes an electrochemical sensing stack over the exposed portion of the first electrode, including a glucose oxidase layer over the layer of sputtered platinum and a glucose limiting membrane over the glucose oxidase layer.

In another embodiment, an analyte sensor includes a polyester substrate, a layer of platinum on the polyester substrate, a protection layer over the layer of platinum, and an electrochemical sensing stack over the layer of platinum.

Another embodiment provides a planar flexible analyte sensor including a polyester base layer and a working electrode and a reference electrode formed from a layer of sputtered platinum on the base layer. Further, the planar flexible analyte sensor includes an insulating dielectric layer over the polyester base layer and layer of sputtered platinum. The insulating dielectric layer leaves a portion of the first electrode exposed and a portion of the second electrode exposed. Also, the planar flexible analyte sensor includes silver/silver chloride ink on the exposed portion of the reference electrode. The planar flexible analyte sensor further includes a glucose oxidase layer over the exposed portion of the working electrode and a glucose limiting membrane over the glucose oxidase layer.

In another exemplary embodiment, a method for fabricating a planar flexible analyte sensor includes sputtering platinum onto a polyester base layer to form a layer of platinum. The method includes patterning the layer of platinum to form working electrodes and additional electrodes. Further, the method includes forming an insulating dielectric layer over the base layer, wherein the insulating dielectric layer is formed with openings exposing portions of the working electrodes and portions of the additional electrodes. Also, the method includes partially singulating individual sensors from the base layer, wherein each individual sensor is connected to the base layer by a tab. The method further includes depositing an enzyme layer over the exposed portions of the working electrodes and coating the working electrodes with a glucose limiting membrane.

Another exemplary embodiment provides a method for fabricating a planar flexible analyte sensor. The method includes providing a polyester base layer with a first side sputtered with a layer of platinum and with a second side opposite the first side. The method includes patterning the layer of platinum to form working electrodes. Also, the method includes forming an insulating dielectric layer over the first side of the base layer, wherein the insulating dielectric layer is formed with openings exposing portions of the working electrodes. The method further includes printing silver/silver chloride ink over the second side of the base layer. The method also includes partially singulating individual sensors from the base layer, wherein each individual sensor is connected to the base layer by a tab. The method includes depositing an enzyme layer over the exposed portions of the working electrodes and coating the working electrodes with a glucose limiting membrane.

In another embodiment, a method for fabricating analyte sensors in a roll-to-roll process includes providing a roll of a polyester substrate having a first side coated with a layer of platinum. The method feeds the polyester substrate from the roll to an electrode patterning stage. Further, the method includes patterning the layer of platinum to form working electrodes and reference electrodes. The method feeds the polyester substrate to an insulation stage. The method includes forming an insulating dielectric layer over the polyester substrate. The method feeds the polyester substrate to an insulation curing stage. The method includes curing the insulating dielectric layer. The method feeds the polyester substrate to an ink printing stage. The method includes depositing silver/silver chloride ink over the reference electrodes. The method feeds the polyester substrate to a drying stage. The method includes drying the silver/silver chloride ink. The method feeds the polyester substrate to a punching stage. The method includes punching the polyester substrate to form ribbons, wherein each ribbon is connected to a remaining polyester substrate web by a tab, and wherein each sensor includes a working electrode and a reference electrode. The method feeds the remaining polyester substrate to an enzyme deposition stage. The method includes depositing an enzyme layer over the working electrodes. The method feeds the remaining polyester substrate to an enzyme curing stage. The method includes curing the enzyme layer. The method feeds the remaining polyester substrate to a membrane formation stage. The method includes coating the working electrodes with a glucose limiting membrane.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description. Also, while the preceding background discusses glucose sensing and exemplary analyte sensors are described as glucose sensors herein, such description is for convenience and is not limiting. The claimed subject matter may include any type of analyte sensor utilizing an embodiment of the sensor electrodes described herein.

Blood-glucose measurements may be employed in infusion systems for regulating a rate of fluid infusion into a body. In particular circumstances, a control system may be adapted to regulate a rate of insulin, glucagon, and/or glucose infusion into a body of a patient based, at least in part, on a glucose concentration measurement taken from a body (e.g., from an analyte sensor such as a glucose sensor).

According to certain embodiments, examples of analyte sensors as described herein may be implemented in a hospital environment to monitor levels of glucose in a patient. Alternatively, according to certain embodiments, examples of analyte sensors as described herein may be implemented in non-hospital environments to monitor levels of glucose in a patient. Here, a patient or other non-medical professional may be responsible for interacting with analyte sensors.

To maintain healthy glucose levels, a person with type 1 diabetes may manage their glycemia by monitoring blood glucose levels, controlling diet, exercise, and self-administering appropriate amounts of insulin at appropriate times. Deviations from such glycemic management, such as skipping an insulin bolus at meal time or underestimating the carbohydrate content of a meal may bring about prolonged hyperglycemia. Likewise, receiving too much insulin (e.g., by over-bolusing) for a given blood glucose level and/or meal may bring about severe hypoglycemia. Other external factors, such as exercise or stress, may also contribute to glycemic deviations.

Errors in reading glucose levels may contribute to providing too much or too little insulin. Therefore, sensor accuracy is of utmost concern. Further, sensor accuracy must be maintained during the lifetime of a continuous glucose monitoring device. There is desire for longer life continuous glucose monitoring devices, i.e., continuous glucose monitoring devices that are implanted for a longer duration, such as for seven to fourteen days, or longer. Therefore, in the future, sensor accuracy must be maintained in vivo for seven to fourteen days, or longer. Continuous glucose monitoring sensors provide the ability to continuously track glucose levels in a patient, and to correlate them to his or her physical activity and diet, thereby providing for therapy decisions as well as for adjustments, as necessary.

By more accurately monitoring a patient's glucose level and maintaining appropriate infusion rates, extreme glycemic variations may be reduced or avoided altogether. This may provide a patient with improved glycemic control in circumstances in which they would otherwise be exposed to undesirable extremes of glycemia.

Embodiments herein provide for improved accuracy as compared to current commercialized sensors, and will reduce sensor cost through new manufacturing processes. For example, sensors herein may utilize excimer-patterned electrodes formed from platinum-sputtered layers on polyester film substrates.

Figure 1:
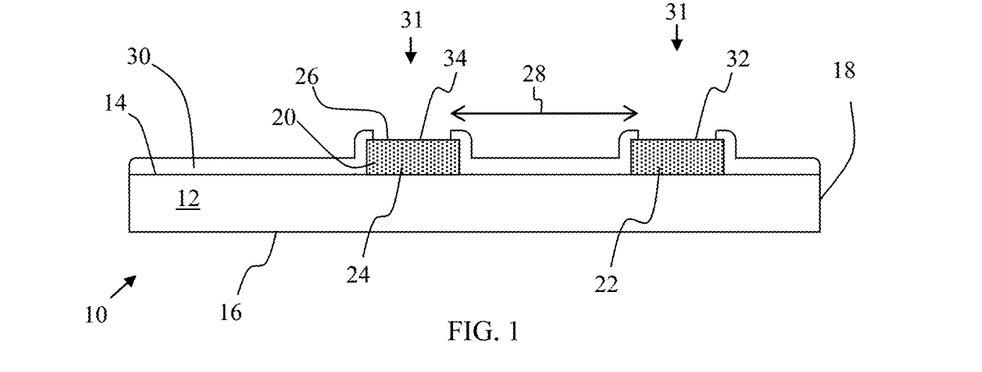
FIG. 1 is a side cross-sectional view of a partially fabricated analyte sensor in accordance with an embodiment.

FIG. 1 is a cross sectional view of an example analyte sensor 10 for use with a glucose control system in accordance with an embodiment. Particular embodiments of the analyte sensor 10 include a planar flexible polymeric base layer 12, such as a polyester film or substrate. As shown, the base layer 12 includes a first side 14 and an opposite second side 16 and an end 18. An exemplary base layer 12 has a thickness of from about 25 micrometers (μm) (about 1 mil) to about 381 μm (about 15 mil), such as about 178 μm (about 7 mil) or about 254 μm (about 10 mil).

In certain embodiments, the base layer 12 has a surface roughness of from about 1 nm to about 240 nm, for example, from 5 nm to about 80 nm, such as from about 5 to 10 nm, or from about 10 to 20 nm, or from about 20 to 30 nm, or from about 30 to 50 nm, or from about 50 to 70 nm.

Further, a platinum layer 20 is formed on the first side 14 of the base layer 12. In exemplary embodiments, the platinum layer 20 is formed by sputtering platinum onto the first side 14 of the base layer 12. An exemplary platinum layer 20 may have a thickness of from about 5 to about 120 nm, such as from about 10 to about 50 nm.

During in vivo use, platinum is challenged by the immune response that the body elicits upon sensor implantation. For example, the constant mechanical forces exerted by the body tissue around the implant may compromise the adhesion of platinum to polyester substrates. Therefore, the first side 14 of the base layer 12 may undergo surface modification to modulate adhesion between the platinum layer 20 and the base layer 12. Such surface modification may allow for controlled and reproducible tuning of electrode surface area to improve in vivo sensor performance. Also, surface modification may provide for grafting functional moieties to the first side 14 of the base layer 12 to increase adhesion. Surface modification may be performed by plasma pretreatment of the base layer 12. Other processes may be performed to roughen the surface of the base layer 12.

Also, the platinum layer 20 may be formed with an exterior surface 26 having a selected surface roughness. Sputtering of platinum on polyester substrates is a well-known process that yields high uniformity and reproducibility in the surface roughness of the exterior surface 26. Surface roughness of the exterior surface 26 of platinum layer 20 is a controlling factor for electrode surface area. Through adjusting the process parameters of the platinum sputtering process, the surface roughness of the exterior surface 26 of platinum layer 20, and electrodes, may be controlled.

As shown, the analyte sensor 10 is formed with electrodes necessary for sensor operation. For example, the analyte sensor 10 may be formed with working, reference, and counter electrodes. In FIG. 1, two electrodes 22 and 24 are illustrated for simplicity; however, the analyte sensor 10 may include one or more working, reference, and counter electrodes. In certain embodiments, the analyte sensor 10 may include pairs of working electrodes and counter electrodes.

The electrodes 22 and 24 may be formed by patterning the platinum layer 20. For example, a laser ablation process may be performed to pattern the platinum layer 20. In an exemplary embodiment, an excimer laser, such as a 248 nanometer excimer laser, is utilized to pattern the platinum layer 20 with ultraviolet light to form the electrodes 22 and 24. Laser ablation provides for high throughput during sensor fabrication processing and is highly reproducibly. For example, in certain embodiments, electrodes for eighteen analyte sensors 10 can be patterned per second by the laser ablation process.

As shown, the analyte sensor 10 further includes an insulating dielectric layer 30 over the first side 14 of the base layer 12. An exemplary insulating dielectric layer 30 may be a polymer that is crosslinked by ultra violet radiation or by a thermal process such that after crosslinking the insulation dielectric is impermeable to solvents and water and other electrochemically active constituents in the analyte containing fluid. The insulating dielectric layer 30 is provided to prevent diffusion of the electrochemically active constituent to the electrode's electrochemically active surface for the purpose of accurately controlling the electrode signal level.

The electrode signal is proportional to the surface area that is exposed to the analyte containing fluid. An insulating dielectric layer 30 that is impermeable to electrochemically active constituents in the analyte containing fluid can be applied and patterned to define the electrode's electrochemically active surface area. Methods of applying and patterning the dielectric layer include screen printing, digital drop on demand, transfer pad printing, gravure coating or other photolithography patterned coating method known to those skilled in the art.

An exemplary insulating dielectric layer 30 can be an acrylic polymer that is thermally crosslinked. An exemplary insulating dielectric layer 30 has a thickness of from about 1 µm to about 20 µm, such as about 7 µm.

In exemplary embodiments, the insulating dielectric layer 30 is formed by screen printing or rotary printing the insulating dielectric material. In certain embodiments, the insulating dielectric layer 30 is patterned or otherwise formed with openings 31 that leave a portion 32 of electrode 22 exposed and a portion 34 of electrode 24 exposed. In other words, after formation of the insulating dielectric layer 30, the portion 32 of the electrode 22 and the portion 34 of the electrode 24 are not covered by the insulating dielectric layer 30. The openings 31 define the geometric surface area of the electrodes 22 and 24. In other words, the exposed portions 32 and 34 of the electrodes 22 and 24 are the geometric surface areas of the electrodes 22 and 24.

In exemplary embodiment, electrode 22 is a working electrode, electrode 24 is a counter electrode, and the width of the insulating dielectric layer 30 is modulated so that the end-to-end distance 28 between the openings 31 of platinum working electrode 22 and platinum counter electrode 24 is changed to improve overall sensor sensitivity and to lower sensor dependence on oxygen concentration. The end-to-end distance between the openings can be from about 5 microns to about 200 microns, such as from about 15 microns to about 100 microns, for example about 50 microns.

Thus, FIG. 1 may be considered to illustrate a single pair of working and counter electrodes 22 and 24 with a selected intrapair distance 28. It is contemplated that the sensor 10 include multiple working electrodes (WE) and counter electrodes (CE), wherein each WE/CE pair has a specific, independently selected end-to-end distance 28 between the openings 31 of the working and counter electrodes. In other words, the sensor 10 may be provided with a plurality of WE/CE pairs, each having an independently selected intrapair distance. While WE/CE pairs may be provided with different intrapair distances from one another, certain WE/CE pairs may have a same intrapair distance.

The differential response from these multiple WE/CE pairs can provide insights on sensor dependence on oxygen which can used to calibrate the sensor performance against sensitivity drifts. For example, sensitivity can drift due to sensor degradation caused by exposure to various electroanalytical species such as oxygen radicals. In addition, post-implantation effects such as biofouling and foreign body response also contribute to passivation of the electro catalytic activity of the electrode.

Figure 2:
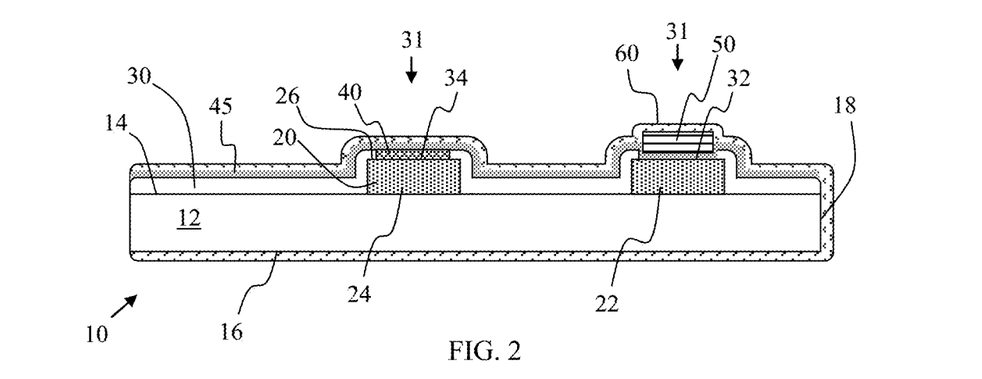
FIG. 2 is a side cross-sectional view of an analyte sensor in accordance with an embodiment.

In FIG. 2, further processing may be performed on the analyte sensor 10. In FIG. 2, electrode 22 is processed to form a working electrode and electrode 24 is processed to form a reference electrode (as noted above, multiple electrodes are not illustrated simply for purposes of clarity). For a reference electrode 24, a silver/silver chloride (Ag/AgCl) ink layer 40 is formed over the electrode 24. The silver/silver chloride layer 40 may be selectively deposited by screen printing or rotary printing. Unlike conventional electrodeposition or electro-oxidation processes, silver chloride loading is not limited by the surface area of the electrode when screen printing or rotary printing silver/silver chloride ink. In an exemplary embodiment, the silver/silver chloride layer 40 is overloaded such that the amount of AgCl is always in excess as compared to what is needed for sensor operation over 14 days. In some cases the ratio of AgCl to Ag is greater than 1 and can be from about 1 to about 10, such as about 5. It is noted that the silver/silver chloride (Ag/AgCl) ink layer 40 may be formed before or after formation of the insulating dielectric layer 30 but a preferred embodiment includes depositing the silver/silver chloride ink before the dielectric material In an exemplary embodiment, the silver/silver chloride ink has a formulation of micro and nano particles of silver and silver chloride in a polymeric binder to enhance overloading of the silver/silver chloride ink during screen printing or rotary printing. In an exemplary embodiment, the silver/silver chloride layer has a thickness (or height) of from about 5 µm to about 50 µm, such as about 10 µm. In an exemplary embodiment, the reference electrode is made up of metal oxide micro and nanoparticles loaded within a polymeric binder. An exemplary metal oxide is Iridium Oxide.

As noted above, during in vivo use, platinum is challenged by the immune response that the body elicits upon sensor implantation. For example, degradation of the platinum may be induced by biofouling and the body's immune response. Unless provided for, the platinum may not withstand the degradation induced by biofouling and the body's immune response. Therefore, the analyte sensor 10 may be provided with a protection layer 45 over the first side 14 of the base layer 12 for protecting the platinum from biofouling and other immune response degradation. An exemplary protection layer 45 may be a hydrophilic hydrogel layer and can be made from a wide variety of materials known to be suitable for such purposes, e.g., polyvinyl alcohol, poly (N-isopropylacrylamide), poly (N-vinylpyrrolidone), polyethylene glycol, polyurethane, poly acrylic acid, cellulose acetates, Nafion, polyester sulfonic acids hydrogels or any other suitable hydrophilic membranes known to those skilled in the art An exemplary protection layer 45 has a thickness of from about 5 nm to about 200 nm, such as about 50 nm. As shown in FIG. 2, the protection layer 45 covers the entire top side 14 of the base layer 12 and completely encapsulates the platinum layers of the electrodes 22 and 24.

In exemplary embodiments, the protection layer 45 is formed by screen printing, rotary printing, spray coating, dip coating, spin coating or brush coating. In certain embodiments, the diffusion properties of the protection layer 45 are carefully controlled so that the magnitude of the sensor signal is not compromised due to smaller diffusion coefficients that will not let hydrogen peroxide pass through, leading to minimal or no signal as per Equation 2 above. In such embodiment, hydrophobic moieties such as acrylate polymers or surfactants or oxygen loading species (such as fluorocarbon compounds) or oxygen bearing enzymes such as myoglobin or hemoglobin or oxygen generating enzymes such as catalase are incorporated within the hydrogel layer to improve adhesion and tune permeability to hydrogen peroxide and oxygen.

FIG. 2 illustrates the silver/silver chloride layer 40 formed before the protection layer 45 such that the silver/silver chloride layer 40 is disposed under the protection layer 45. However, it is noted that the order of formation may be reversed, such that the protection layer 45 lies under the silver/silver chloride layer 40.

In FIG. 2, the analyte sensor 10 further includes an electrochemical sensing stack 50 over the exposed portion 32 of the working electrode 22. The electrochemical sensing stack 50 may include a plurality of layers that are not individually illustrated in FIG. 2. In an exemplary embodiment, the electrochemical sensing stack 50 includes an analyte sensing layer, such as an enzyme layer, for example a glucose oxidase layer. An exemplary glucose oxidase layer has an activity of from about 1 KU/mL to about 45 KU/mL, such as from about 5 to about 20 KU/mL, for example about 15 KU/mL. Further, an exemplary glucose oxidase layer has a thickness of from about 3 to about 10 micrometers (μm), such as from about 4 to about 5 μm, for example from about 4.2 to about 4.4 μm, such as about 4.3 μm. In an exemplary embodiment, the enzyme layer is deposited over the working electrode 32 by rotary screen printing. In another embodiment, the enzyme layer is deposited over the working electrode 32 by an aerosol-based drop on demand technology. In another embodiment, the enzyme layer is deposited over the working electrode 32 by spin coating or spray coating. In another embodiment, the enzyme layer is deposited over the working electrode 32 by one of the above mentioned techniques and further crosslinked by ultra violet radiation or exposure to vapors of crosslinking agents such as glutaraldehyde.

In certain embodiments, the electrochemical sensing stack 50 may include additional layers, such as a protein layer. Typically, a protein layer includes a protein such as human serum albumin, bovine serum albumin or the like.

In certain embodiments, the electrochemical sensing stack 50 may include an adhesion promoter layer disposed over the analyte sensing or enzyme layer in order to facilitate contact and/or adhesion between the analyte sensing layer and another overlying layer. The adhesion promoter layer can be made from any one of a wide variety of materials known in the art to facilitate the bonding between such layers. Typically, the adhesion promoter layer includes a silane compound. In alternative embodiments, protein or like molecules in the analyte sensing layer can be sufficiently crosslinked or otherwise prepared to allow the analyte modulating membrane layer to be disposed in direct contact with the analyte sensing layer in the absence of an adhesion promoter layer. In certain embodiments, additional layers such as an interference rejection layer may be included in the electrochemical sensing stack 50. Such layers may be formed by rotary or screen printing or spin coating or spray coating or through chemical vapor deposition. In another embodiment, the adhesion promoter layer is deposited over the working electrode 32 by one of the above mentioned techniques and further crosslinked by ultra violet radiation or exposure to vapors of crosslinking agents such as glutaraldehyde.

Thus, in certain embodiments, the stack 50 includes a protein layer, such as a human serum albumin (HSA) layer, overlying the glucose oxidase layer, and an adhesion promoting layer over the protein layer. In other embodiments, no protein layer or adhesion promoting layer are included in the electrochemical sensing stack 50.

In FIG. 2, the electrochemical sensing stack 50 is shown to further include an analyte modulating layer 60, such as a glucose limiting membrane (GLM) 60, over the enzyme layer. The analyte modulating layer 60 is provided to regulate analyte contact with the analyte sensing layer or enzyme layer. For example, the analyte modulating membrane layer can be a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, Nafion, polyester sulfonic acids (e.g. Kodak AQ), hydrogels or any other suitable membranes known to those skilled in the art. In an exemplary embodiment, the thickness of the glucose limiting membrane 60 is from about 10 to about 30 micrometers (μm), such as from about 18 to about 25 μm, for example from about 20 to about 22 μm, such as about 21 μm.

As shown, the glucose limiting membrane 60 may be formed around the entire end 18 of the analyte sensor 10, i.e., over both the first side 14 and the second side 16 of the base layer 12, including over reference electrodes and counter electrodes. In an exemplary embodiment, the glucose limiting membrane 60 may be formed by dip coating the end 18 of the analyte sensor 10, such that the glucose limiting membrane 60 encapsulates the analyte sensor 10 for insertion into a patient's interstitial fluid.

In addition to the glucose limiting membrane 60, other membranes may be formed over the end 18 of the analyte sensor 10 to suppress the foreign body response upon implantation. For example, a foreign body response (FBR) membrane may be formed over the glucose limiting membrane 60, such as by dip coating the end 18 of the analyte sensor 10.

Figure 3:
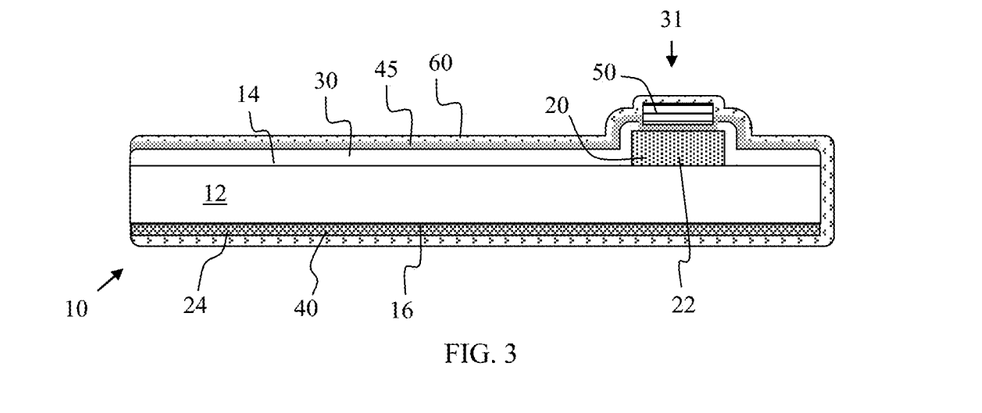
FIG. 3 is a side cross-sectional view of an analyte sensor in accordance with another embodiment.

FIG. 3 illustrates an alternate or additional embodiment of analyte sensor 10. In FIG. 3, the reference electrode 24 is not formed from the platinum layer 20 on the first side 14 of the base layer 12. Rather, the reference electrode 24 is formed on the second side 16 of the base layer 12. Specifically, the reference electrode 24 is formed by a silver/silver chloride ink layer 40 deposited over the second side 16 of the base layer 12. The silver/silver chloride ink may be selectively deposited onto the second side 16 of the base layer 12 by screen printing or rotary printing. In such embodiments, the entire second side 16 could be overprinted or overloaded with silver/silver chloride ink to allow more loading of silver chloride. Further, such an embodiment eliminates positional registration process capability to reduce overall fabrication process error. As shown in FIG. 3, the glucose limiting membrane 60 completely covers the reference electrode 24 formed by the silver/silver chloride ink layer 40 on the second side 16 of the base layer 12.

Figure 4:
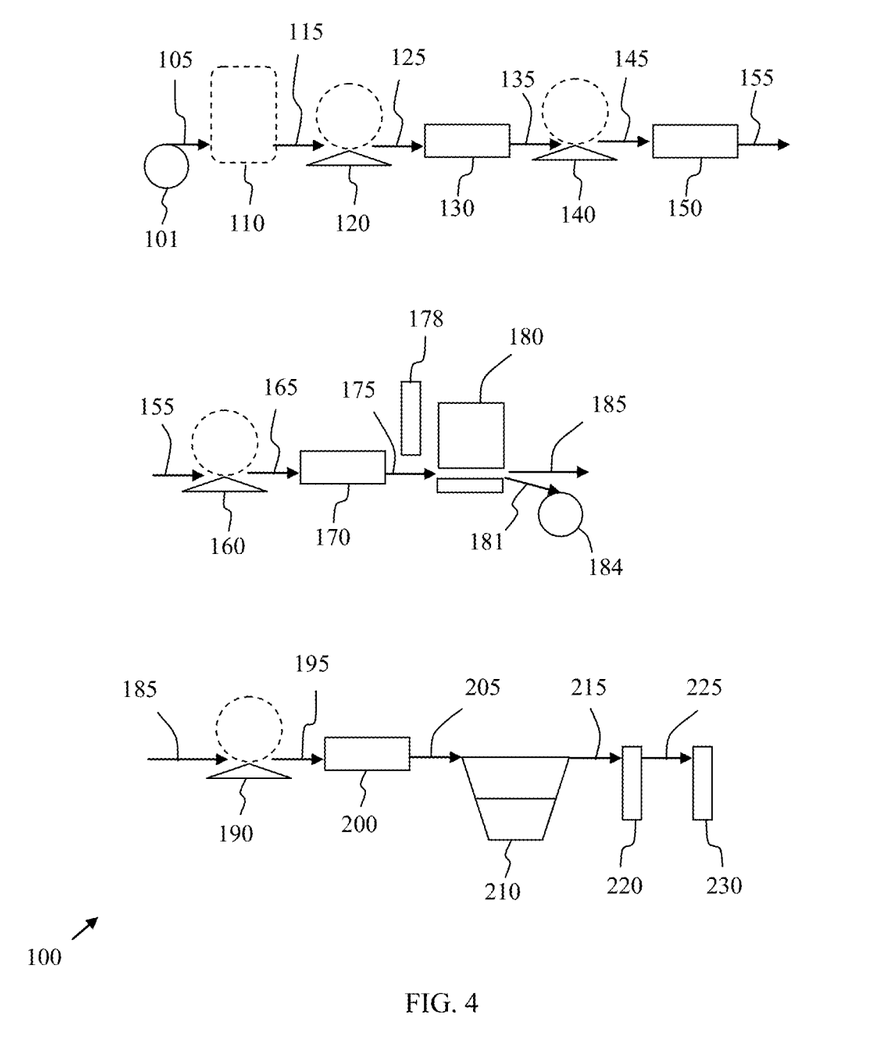
FIG. 4 is a schematic view of a system and method for fabricating an analyte sensor in accordance with an embodiment.

Referring now to FIG. 4, a system 100 and method for fabricating analyte sensors 10 is described. As shown, the system 100 fabricates analyte sensors in a roll-to-roll process by processing a roll 101 of a flexible substrate, such a polyester film, that includes a layer of sputtered platinum as described above. In the system 100, the polyester substrate 105 is fed from the roll 101 to an electrode patterning stage 110. At the electrode patterning stage 110, the layer of platinum is patterned, such as by laser ablation, to form working electrodes and counter electrodes, and optionally reference electrodes, depending on the desired analyte sensors. Then, the polyester substrate 115 is fed from the electrode patterning stage 110 to an insulation stage 120. At the insulation stage 120, an insulating dielectric material is selectively deposited over the polyester substrate 115. For example, an insulating dielectric material may be screen printed or rotary printed over the polyester substrate.

The polyester substrate 125 is then fed from the insulation stage 120 to an insulation curing stage 130 where the insulating dielectric material is cured to form the insulating dielectric layer. For example, an ultraviolet light curing process may be performed. Then, the polyester substrate 135 is fed from the insulation curing stage 130 to an ink printing stage 140. At the ink printing stage 140, silver/silver chloride ink is deposited over the reference electrodes, if such reference electrodes have been formed from the sputtered platinum. Alternatively, the silver/silver chloride ink is deposited over the second side or backside of the polyester substrate to form the reference electrodes. The silver/silver chloride ink may be selectively deposited by screen printing or by rotary printing.

As shown, the polyester substrate 145 is then fed from the ink printing stage 140 to a drying stage 150. At the drying stage 150, the silver/silver chloride ink is dried to form the silver/silver chloride ink layer on the polyester substrate. After drying, the polyester substrate 155 is then fed to a protection layer stage 160 where a protection material is deposited over the polyester substrate 155. Specifically, the protection material is deposited over the entire side of the polyester substrate 155 on which the sputtered platinum electrodes are located. The protection material may be deposited by screen printing or by rotary printing. The polyester substrate 165 is then fed to the curing stage 170 where the protection material is cured to form a protection layer.

The polyester substrate 175 is then fed to a punching stage 180. At the punching stage 180, the polyester substrate is punched, or otherwise cut, to form partially singulated ribbons for forming singulated analyte sensors. For example, the polyester substrate may be laser cut to form the partially singulated ribbons. As shown, the polyester substrate 175 may be passed under a vision alignment device 178 to ensure that the polyester substrate 175 is properly aligned for punching. After punching, each ribbon is still connected to a remaining polyester substrate web by a tab. In exemplary embodiments, each ribbon or analyte sensor includes a working electrode and a reference electrode. Specifically, each ribbon or analyte sensor includes the desired number of working electrodes, reference electrodes and counter electrodes without further electrode formation.

A punched out or scrap portion 181 of the polyester substrate 175 may be wound up into a roll 184 from the punching stage 180. The remaining polyester substrate 185 (including the singulated analyte sensors in the form of ribbons) is fed to an enzyme deposition stage 190. At the enzyme deposition stage 190, an enzyme, such as glucose oxidase, is deposited over the working electrodes. For example, the enzyme may be screen printed or rotary printed onto the polyester substrate. Alternatively, the enzyme may be deposited by an aerosol-based drop on demand technology. In addition to the enzyme, other materials for forming an electrochemical sensing stack may be deposited over the polyester substrate at the enzyme deposition stage 190.

Then, the polyester substrate 195 is fed to an enzyme curing stage 200. At the enzyme curing stage 200, the enzyme (and other deposited materials) is cured, such as by an ultraviolet light photo-initiated curing process. During curing, the enzyme crosslinks and becomes immobilized. The polyester substrate 205 may then be fed to a membrane formation stage 210. At the membrane formation stage 210, the end of each ribbon may be coated with a glucose limiting membrane and other desired membranes. For example, the end of each ribbon may be dip coated or slot coated to form the desired membranes.

In certain embodiments, the system 100 may terminate the roll-to-roll processing at this stage and produce a polyester substrate 215 including individual analyte sensors, in the form of ribbons connected to the polyester substrate web, ready for further integration with production of a glucose monitoring system. Alternatively, roll-to-roll processing may continue with processing the individual analyte sensors on polyester substrate 215. Specifically, the individual analyte sensors on polyester substrate 215 may be processed through a functionality check stage 220. At the functionality check stage 220, each analyte sensor is exposed to a buffer solution containing glucose, and the sensor's signal-time profile is recorded and evaluated.

Further, the polyester substrate 225 may be removed from the functionality check stage 220 and may be fed to a singulation stage 230. At the singulation stage 230, the individual analyte sensors, in the form of ribbons connected to the polyester substrate web, may be singulated through complete separation from the polyester substrate web. The singulation stage 230 may be part of a final system assembly and packaging system separate from the roll-to-roll processing system 100 described here.

It is noted that the system 100 of FIG. 4 may include additional elements, such as idler wheels, driven wheels, vacuum boxes, and additional, alternative, or repetitive process stages, for the fabrication of the analyte sensors.

Figure 5:
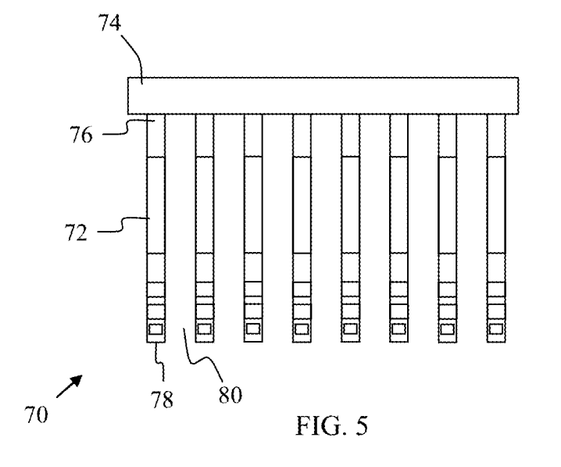
FIG. 5 is a top view of a partially singulated substrate as fabricated according to the method of FIG. 4.

FIG. 5 is a top view of a partially singulated substrate 70, as fabricated according to the method of FIG. 4. Specifically, the partially singulated substrate 70 is illustrated as formed after being punched out, after enzyme layer formation, and after membrane formation, such as after membrane formation stage 210 or after functionality check stage 220 of FIG. 4. Further, the partially singulated substrate 70 is illustrated as before complete separation of analyte sensors from the polyester substrate at singulation stage 230 of FIG. 4.

As shown in FIG. 5, the partially singulated substrate 70 includes individual analyte sensors 72, in the form of ribbons. Each individual analyte sensor 72 is connected to the polyester substrate web 74 by a tab at end 76. Complete singulation and separation of the individual analyte sensors 72 may occur by severing at each tab at end 76. As shown, each analyte sensor 72 terminates at an end 78. End 78 may be dipped or otherwise coated with the membrane-forming materials at membrane formation stage 210 of FIG. 4. The gaps 80 between adjacent analyte sensors 72 are formed during the punching out process by removal of portions of the polyester substrate, such as the punched out or scrap portion 181 in FIG. 4.

Figure 6:
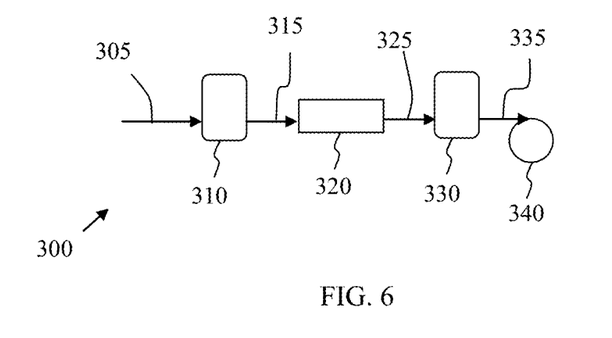
FIG. 6 is a schematic view of a system and method for fabricating the platinum-sputtered substrate for use in the method of FIG. 4 in accordance with an embodiment.

FIG. 6 illustrates a system 300 and method for fabricating the platinum-sputtered polyester substrate that is introduced in FIG. 4 on roll 110. In FIG. 6, a polyester substrate 305 is provided. The polyester substrate 305 may be introduced to a polyester surface modification stage 310. At the polyester surface modification stage 310, the surface of a side or both sides of the polyester substrate 305 is modified. Specifically, the polyester surface may be roughened to improve adhesion between the polyester and the platinum layer to be formed thereon. Also, polyester surface modification may provide for grafting functional moieties to the surface to increase adhesion. Surface modification may be performed by plasma pretreatment of the polyester substrate 305. Other processes for surface modification may include electric discharge, surface grafting, flame treatment, UV irradiation or wet chemical etching.

Other processes may be performed to roughen the surface of the polyester substrate 305 and include wet chemical etching, hydrolysis in a basic solution, acid washing or laser irradiation.

As shown, the polyester substrate 315 is then fed to a platinum deposition stage 320. At the platinum deposition stage 320, platinum is deposited onto a side of the polyester substrate 315. For example, platinum may be sputtered onto the polyester substrate. Sputtering is a physical vapor deposition method. Sputtering can be carried out using commercially available sputtering reactors using an RF (radio frequency). Magnetron sputtering can also be used. Magnetron sputtering uses a magnetic field to concentrate electrons near the target surface to increase the deposition rate. The thickness of an exemplary sputtered platinum layer is from about 5 to about 100 nm, for example, from about 10 to about 50 nm. When multiple layers are deposited, the total thickness of the layers may have a thickness within the foregoing ranges.

The characteristics of the thin film of platinum that is produced through sputtering vary based on the process parameters, such as characteristics of the platinum sputtering target material, including purity and microstructure, sputtering rate, the energy with which the sputtered platinum atoms reach the polyester substrate, temperature, and/or other parameters.

Control of the process parameters may produce a platinum-sputtered polyester substrate 325 having desired properties. For example, through adjusting the process parameters of the platinum sputtering process, the surface roughness of the exterior surface of the platinum layer may be controlled. Alternatively, the platinum-sputtered polyester substrate 325 may undergo further processing. For example, the platinum-sputtered polyester substrate 325 may be introduced to a platinum surface modification stage 330. At the platinum surface modification stage 330, a plasma surface modification process or other surface modification process may be performed to adjust the surface characteristics of the platinum layer as desired. Thereafter, the platinum-sputtered polyester layer 335 may be wound on a roll 340 for use in the fabrication method 100 of FIG. 4.

It should be noted that although aspects of the above methods, systems and sensors have been described in particular orders and in particular arrangements, such specific orders and arrangements are merely examples and claimed subject matter is not limited to the orders and arrangements as described.

Although what are presently considered to be example features have been illustrated and described, it will be understood by those skilled in the art that various other modifications may be made, and equivalents may be substituted, without departing from claimed subject matter. Additionally, many modifications may be made to adapt a particular situation to the teachings of claimed subject matter without departing from central concepts that are described herein. Therefore, it is intended that claimed subject matter not be limited to particular examples disclosed, but that such claimed subject matter may also include all aspects falling within the scope of appended claims, and equivalents thereof.

What is claimed is:

1. A method for fabricating a planar flexible analyte sensor, the method comprising:
   sputtering platinum directly onto a polyester base layer to form a layer of platinum in direct contact with the polyester base layer;
   patterning the layer of platinum to form working electrodes and additional electrodes, wherein the additional electrodes comprise reference electrodes;
   forming an insulating dielectric layer over the polyester base layer, wherein the insulating dielectric layer is formed with openings, wherein the openings lie directly over each electrode and each opening defines a geometric electrode surface area of each electrode;
   printing silver/silver chloride ink over the geometric electrode surface area of each reference electrode;
   forming a protection layer over the insulating dielectric layer, over the geometric electrode surface area of each reference electrode, and over the geometric electrode surface area of each working electrode;
   partially singulating individual sensors from the polyester base layer, wherein each individual sensor is connected to the polyester base layer by a tab, wherein each individual sensor comprises a working electrode and a reference electrode;
   after partially singulating individual sensors from the polyester base layer, depositing an enzyme layer over the geometric electrode surface areas of the working electrodes and coating the working electrodes with a glucose limiting membrane,
   after depositing the enzyme layer over the geometric electrode surface areas of the working electrodes and coating the working electrodes with a glucose limiting membrane, singulating the individual sensors by completely separating each individual sensor from the polyester base layer.

2. The method of claim 1, wherein the protection layer comprises a hydrophilic hydrogel layer.

3. The method of claim 1, wherein the protection layer completely encapsulates the working electrodes and the reference electrodes.

4. The method of claim 1, wherein the protection layer is formed by a screen printing, rotary printing, spray coating, dip coating, spin coating or brush coating process.

5. The method of claim 1, wherein only the layer of platinum separates the silver/silver chloride ink from the polyester base layer.

6. The method of claim 1 wherein sputtering platinum directly onto the polyester base layer to form a layer of platinum comprises modulating adhesion of the platinum to the polyester base layer via surface modification of the polyester base layer.

7. A method for fabricating a planar flexible analyte sensor, the method comprising:
   sputtering platinum directly onto a polyester base layer to form a layer of platinum;
   patterning the layer of platinum to form working electrodes and additional electrodes, wherein the additional electrodes comprise reference electrodes;
   forming an insulating dielectric layer over the polyester base layer, wherein the insulating dielectric layer is formed with openings, wherein the openings lie directly over each electrode and each opening defines a geometric electrode surface area of each electrode;
   printing silver/silver chloride ink over the geometric electrode surface area of each reference electrode;
   forming a protection layer over the insulating dielectric layer, over the silver/silver chloride ink, over the geometric electrode surface area of each reference electrode, and over the geometric electrode surface area of each working electrode;

partially singulating individual sensors from the polyester base layer, wherein each individual sensor is connected to the polyester base layer by a tab, wherein each individual sensor comprises a working electrode and a reference electrode;

after partially singulating individual sensors from the polyester base layer, depositing an enzyme layer over the geometric electrode surface areas of the working electrodes and coating the working electrodes with a glucose limiting membrane, after depositing the enzyme layer over the geometric electrode surface areas of the working electrodes and coating the working electrodes with a glucose limiting membrane, singulating the individual sensors by completely separating each individual sensor from the polyester base layer.

8. The method of claim 7 wherein the protection layer comprises a hydrophilic hydrogel layer.

9. The method of claim 7 wherein the protection layer completely encapsulates the working electrodes and the reference electrodes.

10. The method of claim 7 wherein the protection layer is formed by a screen printing, rotary printing, spray coating, dip coating, spin coating or brush coating process.

* * * * *